United States Patent [19]
McKean et al.

[11] Patent Number: 5,542,594
[45] Date of Patent: Aug. 6, 1996

[54] SURGICAL STAPLING APPARATUS WITH BIOCOMPATIBLE SURGICAL FABRIC

[75] Inventors: Wanda L. McKean, Stamford; Matthew Hain, New Haven; Ilya S. Koyfman, Orange, all of Conn.

[73] Assignee: United States Surgical Corporation, Norwalk, Conn.

[21] Appl. No.: 132,601

[22] Filed: Oct. 6, 1993

[51] Int. Cl.⁶ .................................................. A61B 17/072
[52] U.S. Cl. ...................... 227/178.1; 227/19; 227/180.1
[58] Field of Search ............................. 227/19, 175, 176, 227/177, 178, 179, 180, 181, 175.1, 176.1, 177.1, 178.1, 179.1, 180.1, 181.1

[56] References Cited

U.S. PATENT DOCUMENTS

| | | |
|---|---|---|
| 2,671,444 | 3/1954 | Pease, Jr. . |
| 3,054,406 | 9/1962 | Usher . |
| 3,079,606 | 3/1963 | Bobrov et al. . |
| 3,108,357 | 10/1963 | Liebig . |
| 3,122,140 | 2/1964 | Crowe, Jr. . |
| 3,124,136 | 3/1964 | Usher . |
| 3,272,204 | 9/1966 | Artandi et al. . |
| 3,276,448 | 10/1966 | Kronenthal . |
| 3,284,557 | 11/1966 | Polansky . |
| 3,463,158 | 8/1969 | Schmitt et al. . |
| 3,490,675 | 1/1970 | Green et al. . |
| 3,620,218 | 11/1971 | Schmitt et al. . |
| 3,636,956 | 1/1972 | Schneider . |
| 3,688,317 | 9/1972 | Kurtz . |
| 3,739,773 | 6/1973 | Schmitt et al. . |
| 3,875,937 | 4/1975 | Schmitt et al. . |
| 3,937,223 | 2/1976 | Roth . |
| 4,128,612 | 12/1978 | Roth . |
| 4,132,839 | 1/1979 | Marans et al. . |
| 4,164,046 | 8/1979 | Cooley . |
| 4,186,448 | 2/1980 | Brekke . |
| 4,215,686 | 8/1980 | Gregory et al. . |
| 4,347,847 | 9/1982 | Usher . |
| 4,354,628 | 10/1982 | Green . |
| 4,397,311 | 8/1983 | Kanshin et al. . |
| 4,452,245 | 6/1984 | Usher . |
| 4,520,817 | 6/1985 | Green . |
| 4,520,821 | 6/1985 | Schmitt et al. . |
| 4,548,202 | 10/1985 | Duncan . |
| 4,626,253 | 12/1986 | Broadmax, Jr. . |
| 4,633,861 | 1/1987 | Chow et al. . |
| 4,633,873 | 1/1987 | Dumican et al. . |
| 4,633,874 | 1/1987 | Chow et al. . |
| 4,652,264 | 3/1987 | Dumican . |
| 4,655,221 | 4/1987 | Devereux . |
| 4,702,917 | 10/1987 | Schindler . |
| 4,784,137 | 11/1988 | Kulik et al. . |
| 4,832,686 | 5/1989 | Anderson . |
| 4,838,884 | 6/1989 | Dumican et al. . |
| 4,840,626 | 6/1989 | Linksy et al. . |

(List continued on next page.)

FOREIGN PATENT DOCUMENTS

| | | |
|---|---|---|
| 0334046 | 2/1989 | European Pat. Off. . |
| 0325195 | 7/1989 | European Pat. Off. . |

OTHER PUBLICATIONS

Malm et al., Prevention of postoperative pericardial adhesions by closure of the pericardium with absorbable polymer patches, The Journal of Thoracic and Cardiovascular Surgery, vol. 104, No. 3, pp. 600–607, Sep. 1992.

*Primary Examiner*—Rinaldi I. Rada

[57] ABSTRACT

A surgical stapling apparatus having biocompatible surgical fabric releasably attached thereto for application of the fabric and staples to body tisuse is disclosed. The fabric is releasably held to surfaces of the stapling apparatus through pins, clips or similar securing structures. The biocompatible surgical fabric can be either planar or tubular in configuration. Preferably, both the anvil portion and the fastener ejecting portion of the stapler are at least partially covered with the biocompatible surgical fabric. In use, tissue is disposed between the anvil portion and the stapling portion of the instrument and the instrument is fired. The biocompatible surgical fabric is thereby secured to the tissue and releasably detaches from the stapler upon withdrawal of the stapler from the surgical site.

13 Claims, 9 Drawing Sheets

U.S. PATENT DOCUMENTS

| | | |
|---|---|---|
| 4,865,031 | 9/1989 | O'Keeffe . |
| 4,892,244 | 1/1990 | Fox et al. . |
| 4,905,692 | 3/1990 | More . |
| 4,930,674 | 6/1990 | Barak . |
| 4,955,959 | 9/1990 | Tompkins et al. . |
| 4,960,866 | 10/1990 | Bendix et al. . |
| 4,983,745 | 1/1991 | Muller et al. . |
| 5,002,551 | 3/1991 | Linksy et al. . |
| 5,011,493 | 4/1991 | Belykh et al. . |
| 5,014,899 | 5/1991 | Presty et al. . |
| 5,040,715 | 8/1991 | Green et al. . |
| 5,042,707 | 8/1991 | Taheri . |
| 5,061,281 | 10/1991 | Mares et al. . |
| 5,066,772 | 11/1991 | Tang et al. . |
| 5,079,075 | 1/1992 | Yamasaki et al. . |
| 5,102,983 | 4/1992 | Kennedy . |
| 5,156,797 | 10/1992 | Yamasaki et al. . |
| 5,176,692 | 1/1993 | Wilk et al. . |
| 5,203,864 | 4/1993 | Philips . |
| 5,263,629 | 11/1993 | Trumbull et al. . |
| 5,346,115 | 9/1994 | Perouse et al. ............... 227/179 |
| 5,397,324 | 3/1995 | Carroll et al. ............... 227/19 X |

SURGICAL STAPLING APPARATUS WITH BIOCOMPATIBLE SURGICAL FABRIC

BACKGROUND OF THE INVENTION

1. Field of the Invention

This invention relates to apparatus for applying biocompatible surgical fabric to body tissue and, more particularly, to a surgical stapling apparatus for simultaneously applying biocompatible surgical fabric and a plurality of lines of staples to body tissue.

2. Description of the Related Art

In some surgical operations, surgical supports, e.g., meshes, are employed by surgeons to bridge, repair and/or reinforce tissue defects within a patient, especially those occurring in the abdominal wall, chest wall, diaphragm and other musculo-aponeurotic areas of the body. Surgical supports are disclosed in, e.g., U.S. Pat. Nos. 3,054,406, 3,124, 136, 4,347,847, 4,655,221, 4,838,884 and 5,002,551. During such operations, surgeons employ conventional or known suturing or anchoring techniques to apply such supports to body tissue. For example, U.S. Pat. Nos. 4,452,245 and 5,203,864 describe methods for suturing or anchoring mesh supports to body tissue, especially during hernia repair operations.

Surgical stapling devices are employed by surgeons to sequentially or simultaneously apply one or more rows of surgical fasteners, e.g., staples or two-part fasteners, to body tissue for the purpose of joining segments of body tissue together. Such devices generally consist of a pair of jaws or finger-like structures between which body tissue to be joined is placed. When the instrument is actuated, or "fired," longitudinally moving firing bars contact staple drive members in one of the jaws, thereby pushing surgical staples through the body tissue and into an anvil in the opposite jaw which crimps the staples closed. If tissue is to be removed, a knife blade can be provided to cut between lines of staples. Examples of such instruments are described in U.S. Pat. Nos. 4,354,628, 5,014,899 and 5,040,715, each of which are incorporated herein by reference.

Surgical stapling devices have found widespread application in surgical operations where body tissue must be joined or removed. When operating on thin tissue, such as thin emphysematous lung tissue, it is important to effectively seal the tissue which can be particularly prone to air leakage. Preventing or reducing air leakage can significantly decrease post operative recovery time. Thus, it would be advantageous to provide structure for use with surgical stapling devices which enhances sealing at the surgical site.

SUMMARY OF THE INVENTION

These and other objects and advantages are accomplished herein by providing a surgical stapling apparatus wherein biocompatible surgical fabric is positioned adjacent or attached to a portion of the apparatus so that, upon actuation of the apparatus, both the fabric and a plurality of surgical fasteners are applied to body tissue. The fabric may serve as a bolster or support for the stapled union of tissue and/or impart a hemostatic or other therapeutic effect on the tissue. Briefly stated, the surgical stapling apparatus herein comprises a first jaw structure configured and dimensioned for housing a plurality of surgical fasteners, a second jaw structure disposed in juxtaposed alignment with the first jaw structure for effecting closure of a plurality of surgical fasteners and at least one biocompatible surgical fabric operatively associated with and releasably attached to either or both of the first and second jaw structures, wherein at least a portion of the fabric being disposed between the first and second jaw structures.

As more fully disclosed hereinafter, the biocompatible surgical fabric can be operatively associated with the first jaw structure, i.e., the cartridge frame, and/or the second jaw structure, i.e., the anvil frame, of a surgical stapling apparatus. The fabric can be woven, knit or nonwoven and be manufactured from bioabsorbable or nonbioabsorbable materials.

The term "biocompatible" as applied to the surgical fabric employed in this invention shall be understood to refer to the nontoxic and nonirritating nature of the fabric when maintained in contact with body tissue.

BRIEF DESCRIPTION OF THE DRAWINGS

Preferred embodiments of the invention are described hereinbelow, wherein.

DETAILED DESCRIPTION OF THE PREFERRED EMBODIMENTS

Figure 6:
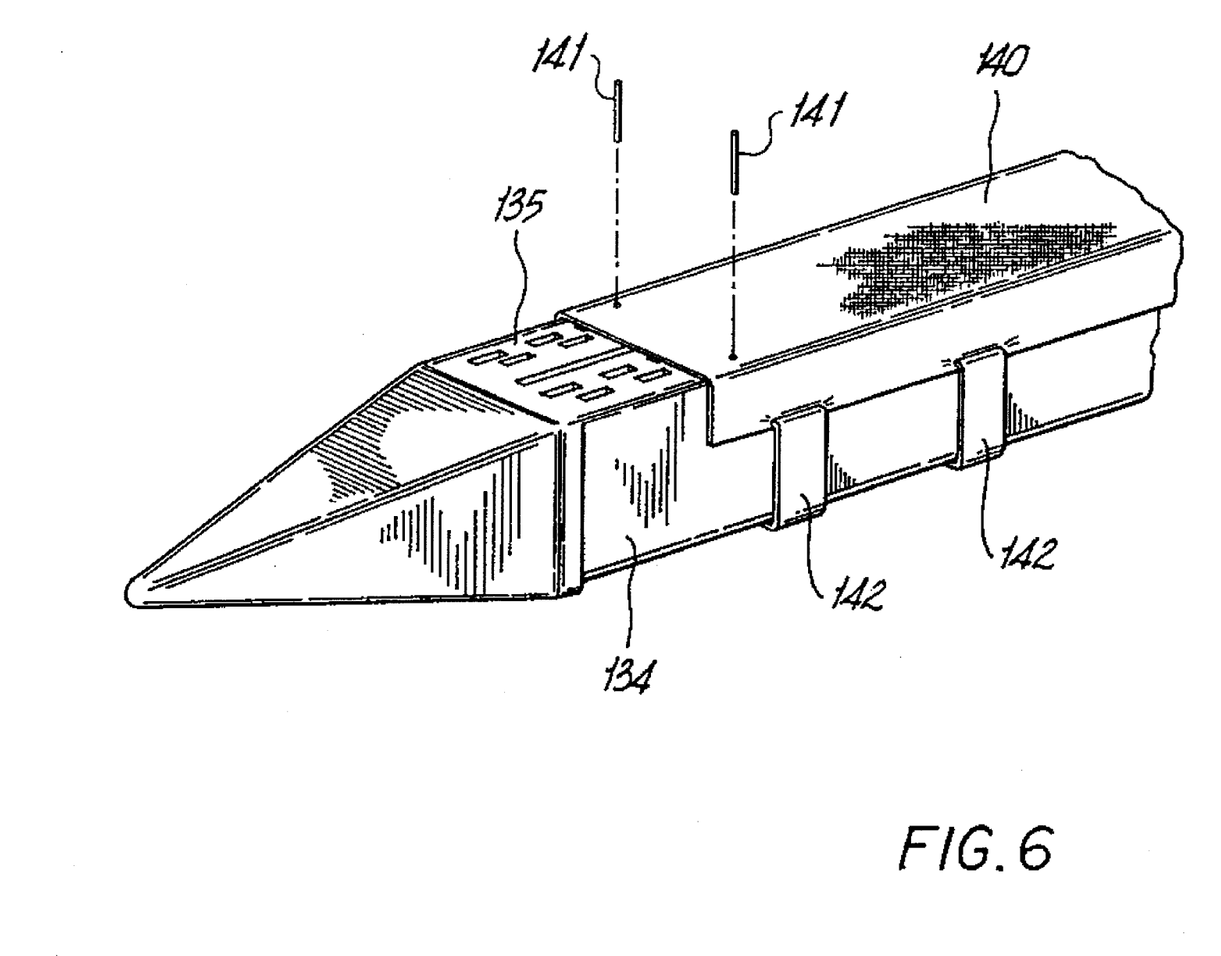
FIG. 6 is an enlarged perspective view depicting a distal portion of the cartridge assembly of a surgical stapling apparatus having the biocompatible surgical fabric depicted in FIG. 2 attached thereto by a plurality of clips.
Figure 7:
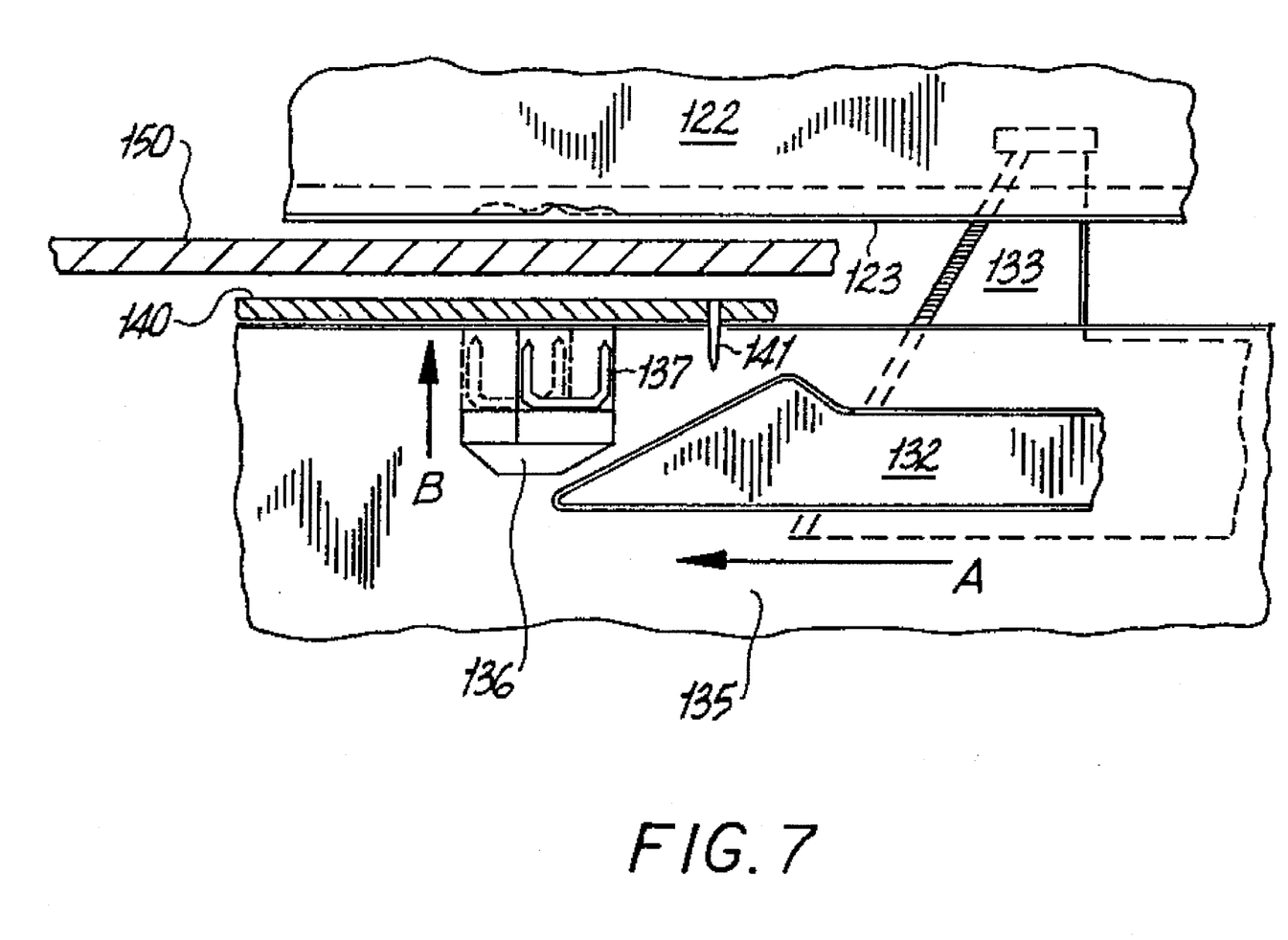
FIG. 7 is an enlarged cut-away side-view of the surgical stapling apparatus of FIG. 1 showing body tissue present between the biocompatible surgical fabric and the anvil portion of the apparatus.
Figure 8:
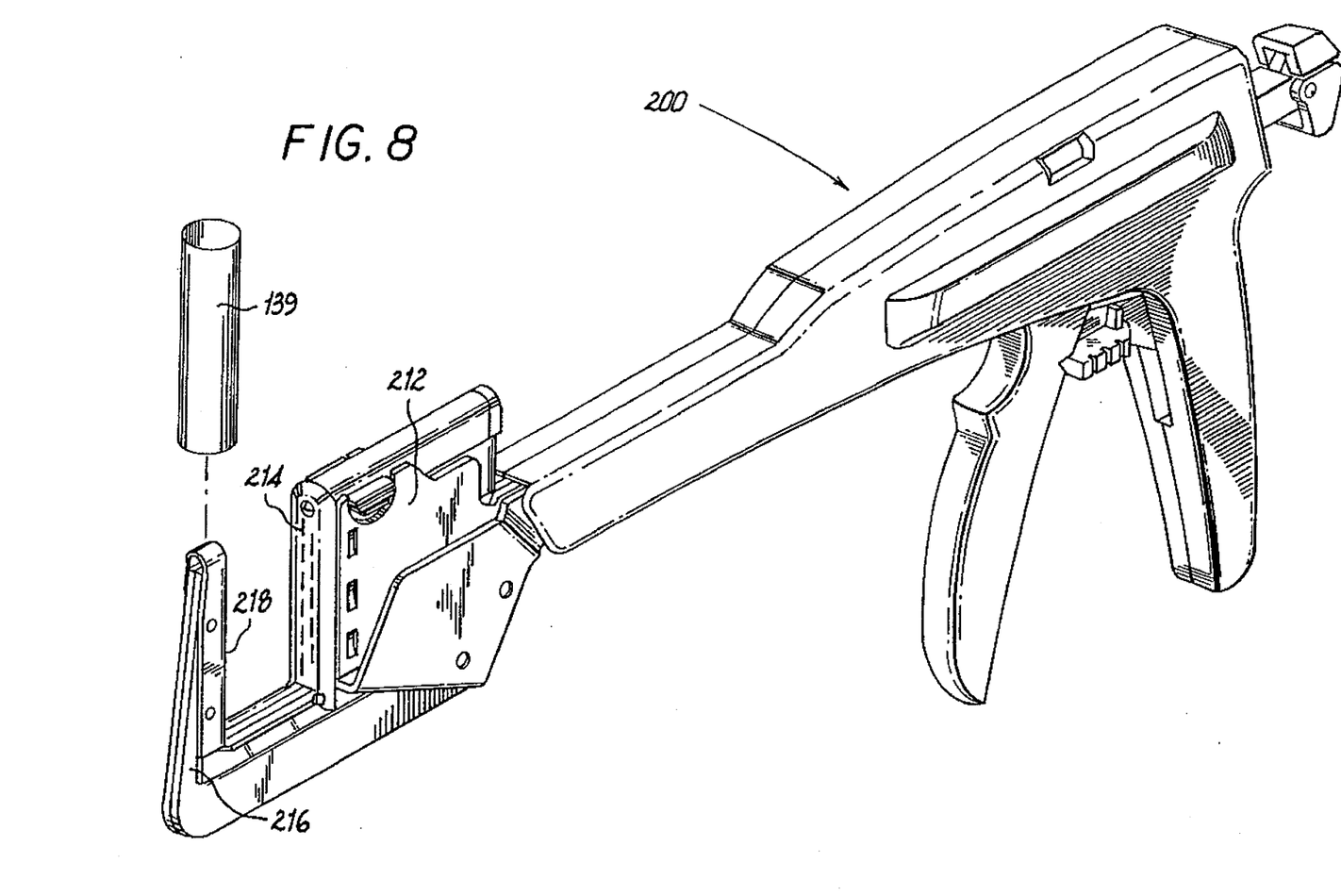
FIG. 8 is a perspective view of a surgical stapling apparatus having a biocompatible surgical fabric which is shaped in a tubular configuration.
Figure 9:
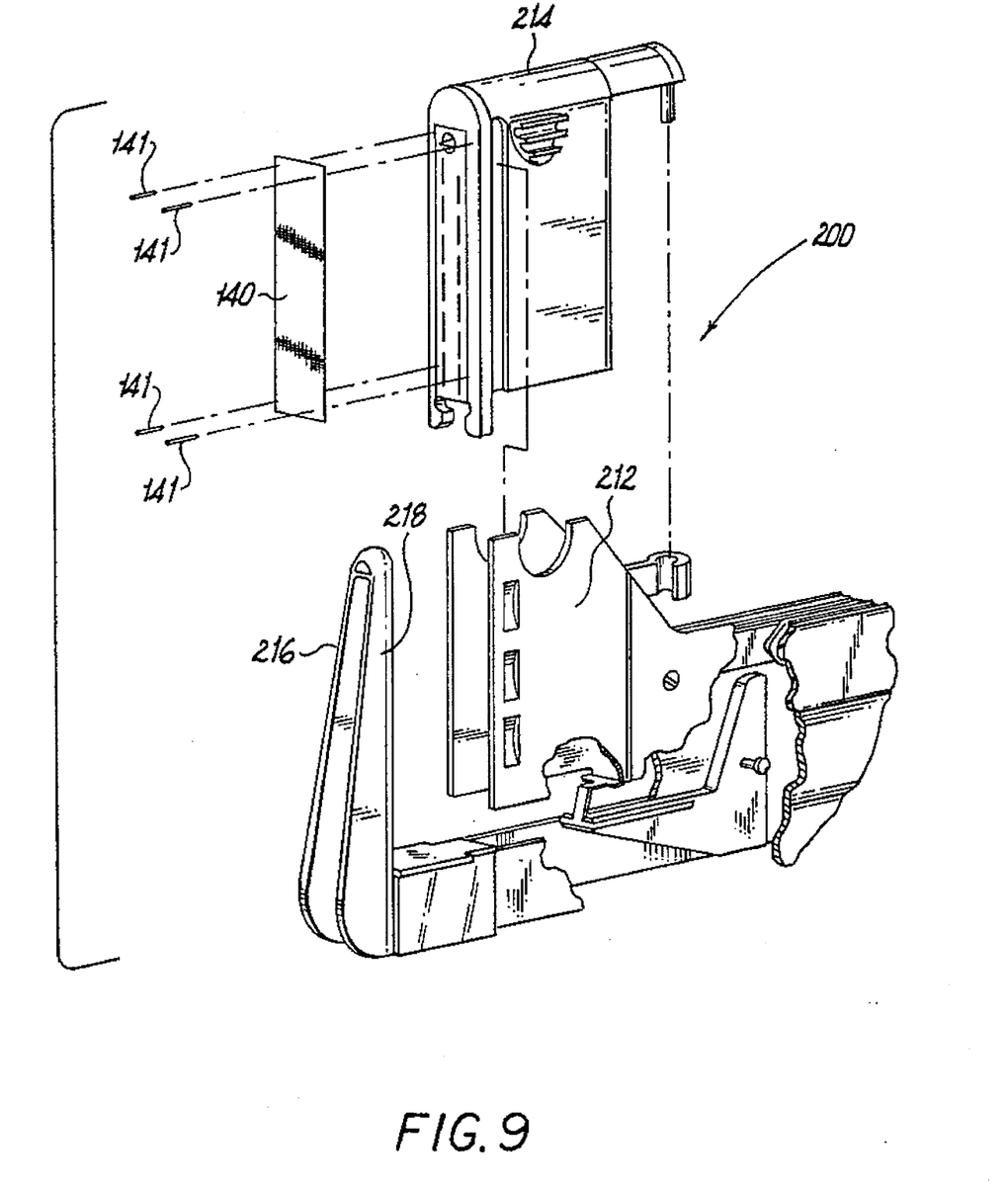
FIG. 9 is a partially cut away exploded perspective view depicting the separated parts of the distal end of the surgical stapling apparatus of FIG. 8.

The surgical stapling apparatus described herein includes a first jaw structure configured and dimensioned for housing a plurality of surgical fasteners, a second jaw structure configured and dimensioned for effecting closure of a plurality of fasteners and at least one biocompatible surgical fabric operatively associated with either of the first and second jaw structures, wherein at least a portion of the fabric is disposed between the first and second jaw structures. The specific design or type of surgical stapling apparatus employed in carrying out this invention is not critical so long as the basic structural elements are present. Thus, e.g., the apparatus can be one that is particularly suited for open surgery or, alternatively, for laparoscopic and/or endoscopic surgery. U.S. Pat. Nos. 5,014,899 and 5,040,715 disclose examples of sequentially firing stapling apparatus for open surgery and endoscopic surgery, respectively. Similarly, the apparatus can be one that applies surgical fasteners simultaneously, as in the case of U.S. Pat. No. 4,354,628. Substantially the same type apparatus as that disclosed and claimed in U.S. Pat. No. 5,014,899, supra, is depicted in FIGS. 1–7. Likewise, substantially the same apparatus disclosed and claimed in U.S. Pat. No. 4,354,678, supra, is depicted in FIGS. 8 and 9. While the embodiments of FIGS. 1–9 herein are preferred, the invention is equally applicable to other surgical stapling apparatus such as that disclosed and claimed in U.S. Pat. No. 5,040,715, supra.

Referring to FIGS. 1–3 and 5, surgical stapling apparatus shown generally at 100 comprises a first jaw structure 110 having a finger-like projection 111 for holding actuating assembly 130. A second jaw structure 120 includes a pair of hinge plates 121 for hingedly connecting to first jaw structure 110 and a finger-like projection 122 for carrying an anvil assembly 123. Anvil assembly 123 is formed of a plate with indentations or depressions which deform the legs of metal staples housed in cartridge assembly 135 of actuating assembly 130. Alternatively, the anvil assembly can include means for holding rows of the retainer portions of two-part surgical fasteners as more fully described in U.S. Pat. No. 5,156,315, the contents of which are hereby incorporated by reference herein.

Disposable loading unit 130 of this embodiment of the present invention is a replaceable unit which includes an actuating assembly consisting of a pusher assembly having a thrust knob 131, cam bars 132 and, optionally, knife blade 133. Disposable loading unit 130 further includes stationary carrier 134 for holding cartridge assembly 135.

Referring now to FIGS. 8 and 9, surgical stapling apparatus 200 comprises a first jaw structure 212 for holding cartridge assembly 214. Cartridge assembly 214 carries a plurality of rows of staples which, upon actuation of the apparatus, substantially simultaneously strike anvil assembly 218 on second jaw member 216 to effect closure. Anvil assembly 218 is formed of a plate with indentations or depressions which deform the legs of metal staples housed in cartridge assembly 214.

Figure 1:
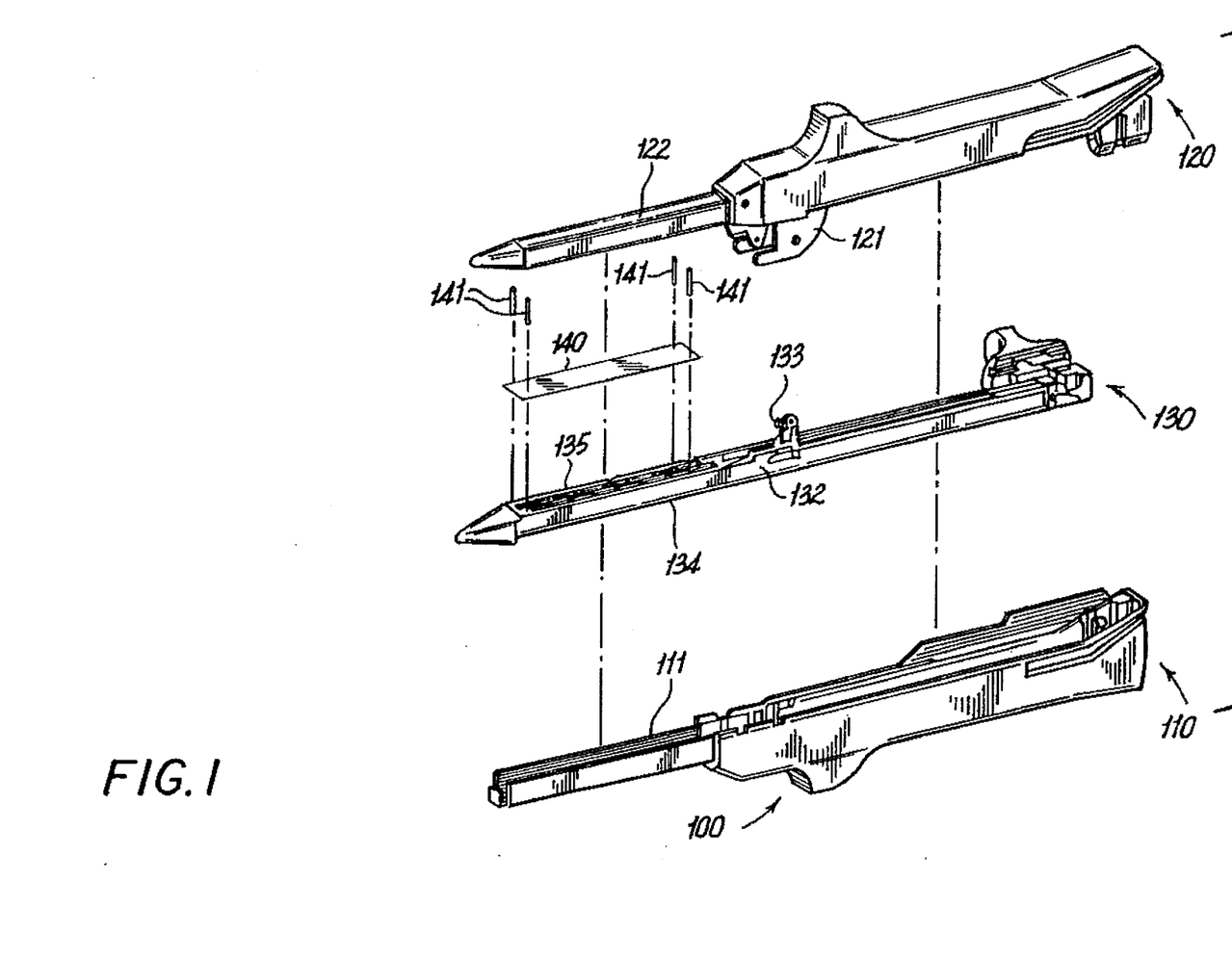
FIG. 1 is a perspective view depicting the separated parts of a surgical stapling apparatus having attached thereto a biocompatible surgical fabric which is dimensioned to substantially conform to the tissue contacting surface dimensions of the cartridge assembly.
Figure 2:
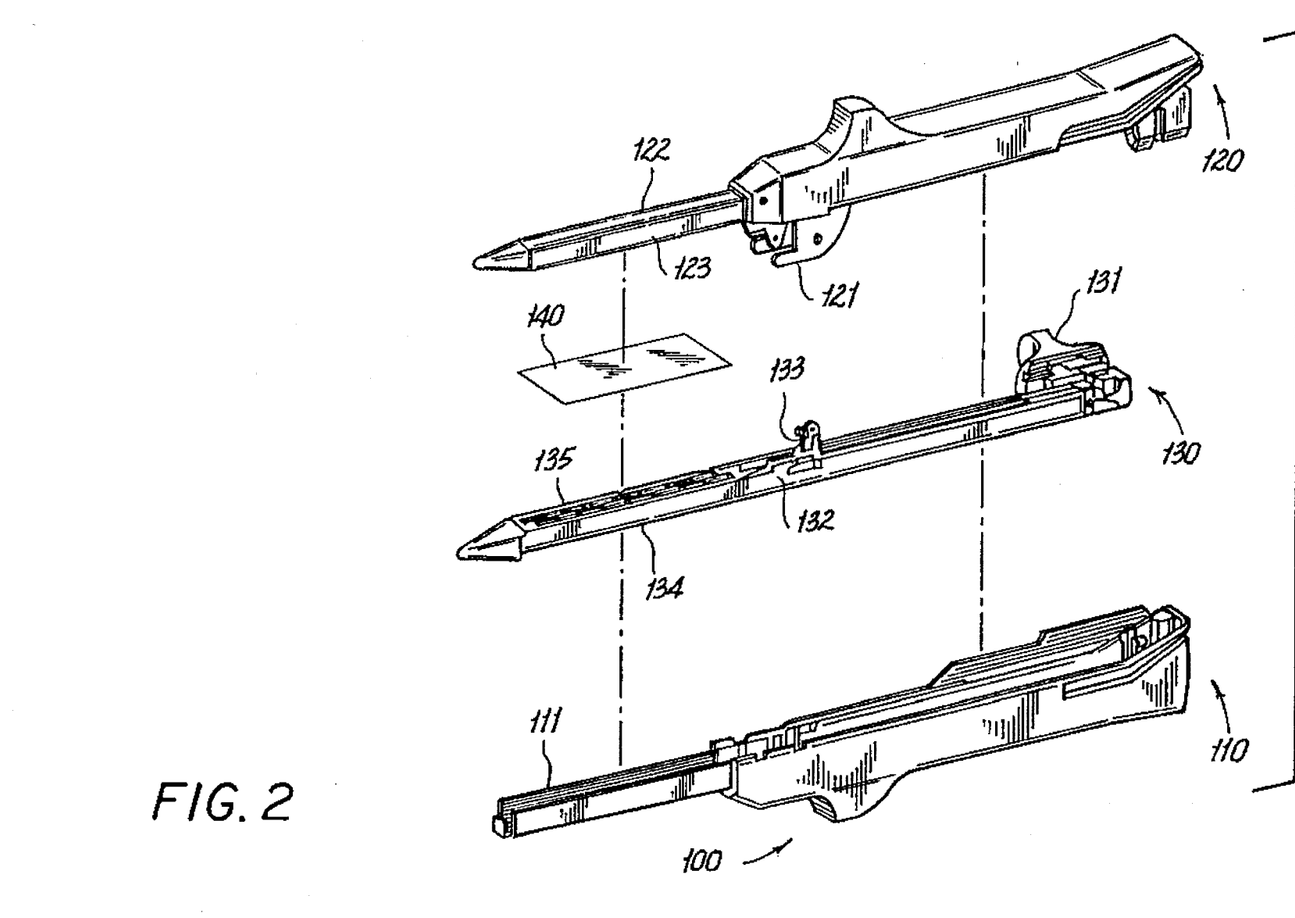
FIG. 2 is a perspective view depicting the separated parts of a surgical stapling apparatus having attached thereto a biocompatible surgical fabric which is configured larger than the tissue contacting surface dimensions of the cartridge assembly.
Figure 3:
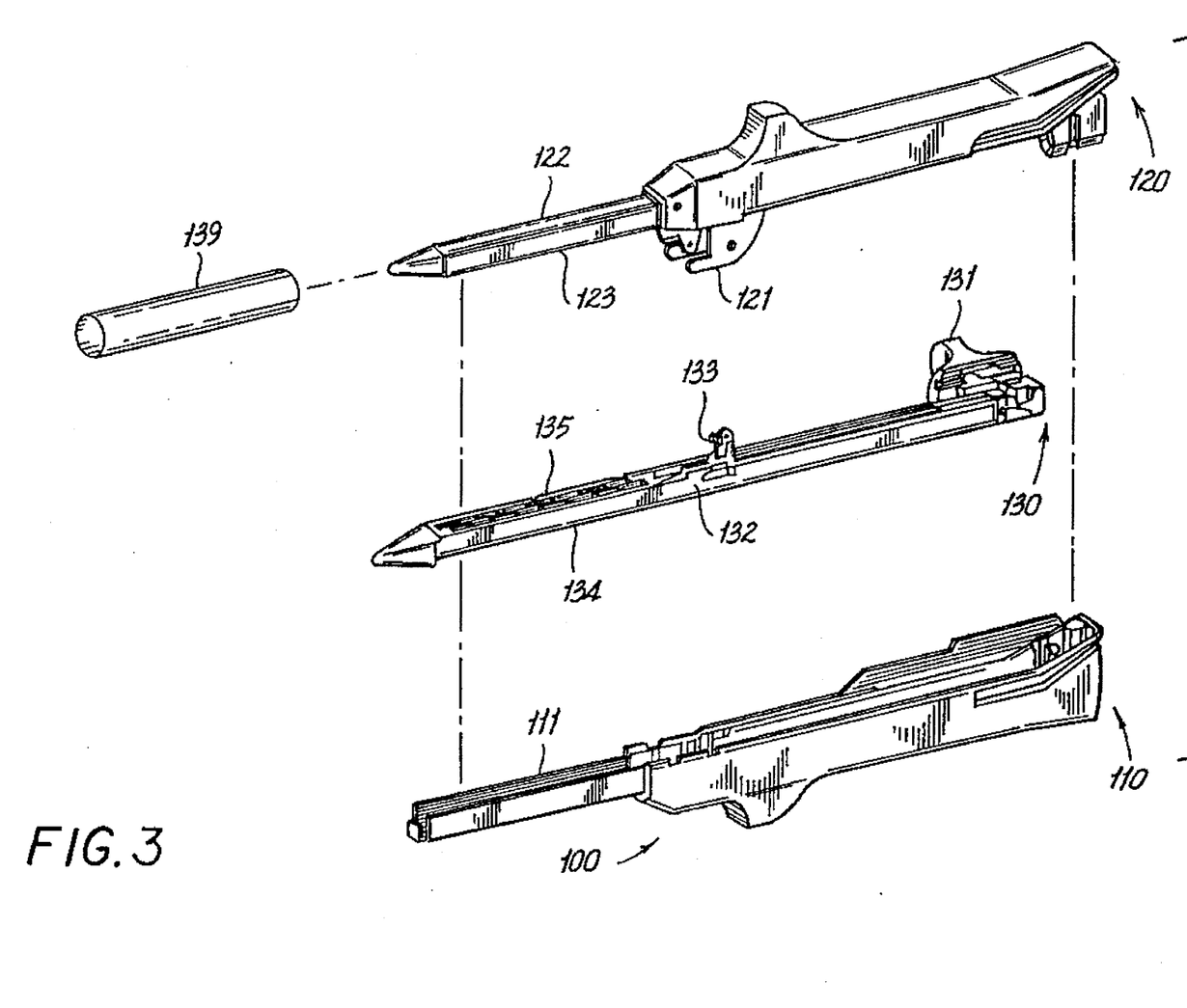
FIG. 3 is a perspective view depicting the separated parts of a surgical stapling apparatus having associated therewith a biocompatible surgical fabric which is shaped in a tubular configuration.
Figure 4:
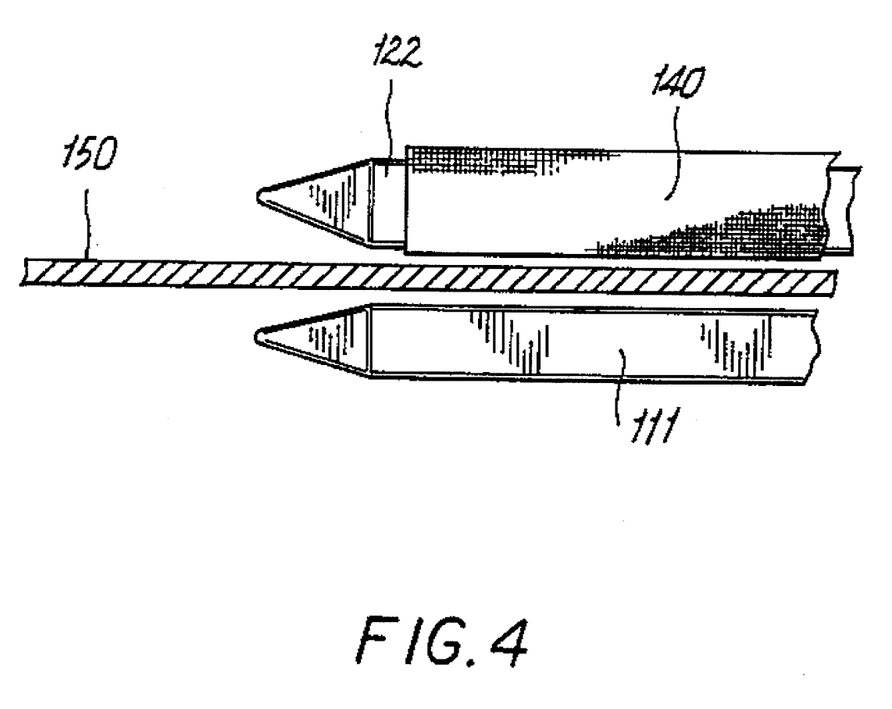
FIG. 4 is an enlarged side-view of the distal end of one embodiment of the surgical stapling apparatus of the present invention engaging body tissue.

Biocompatible surgical fabric 139, 140 is partially or completely disposed between anvil assembly 123 and cartridge assembly 135 as shown, e.g., in FIGS. 1–5, or anvil assembly 218 and cartridge assembly 214, as shown in FIGS. 8 and 9. Fabric 139, 140 can be shaped to any desired configuration. Thus, e.g., in FIGS. 1, 2, 4–7 and 9 fabric 140 is planar while in FIGS. 3, 5 and 8 fabric 139 is tubular. When planar, fabric 140 can be shaped to correspond substantially in size with the tissue contacting surface dimensions of either anvil assembly 123 or cartridge assembly 135 as depicted in FIG. 1 or be wider as depicted in FIGS. 2 and 6.

Figure 5:
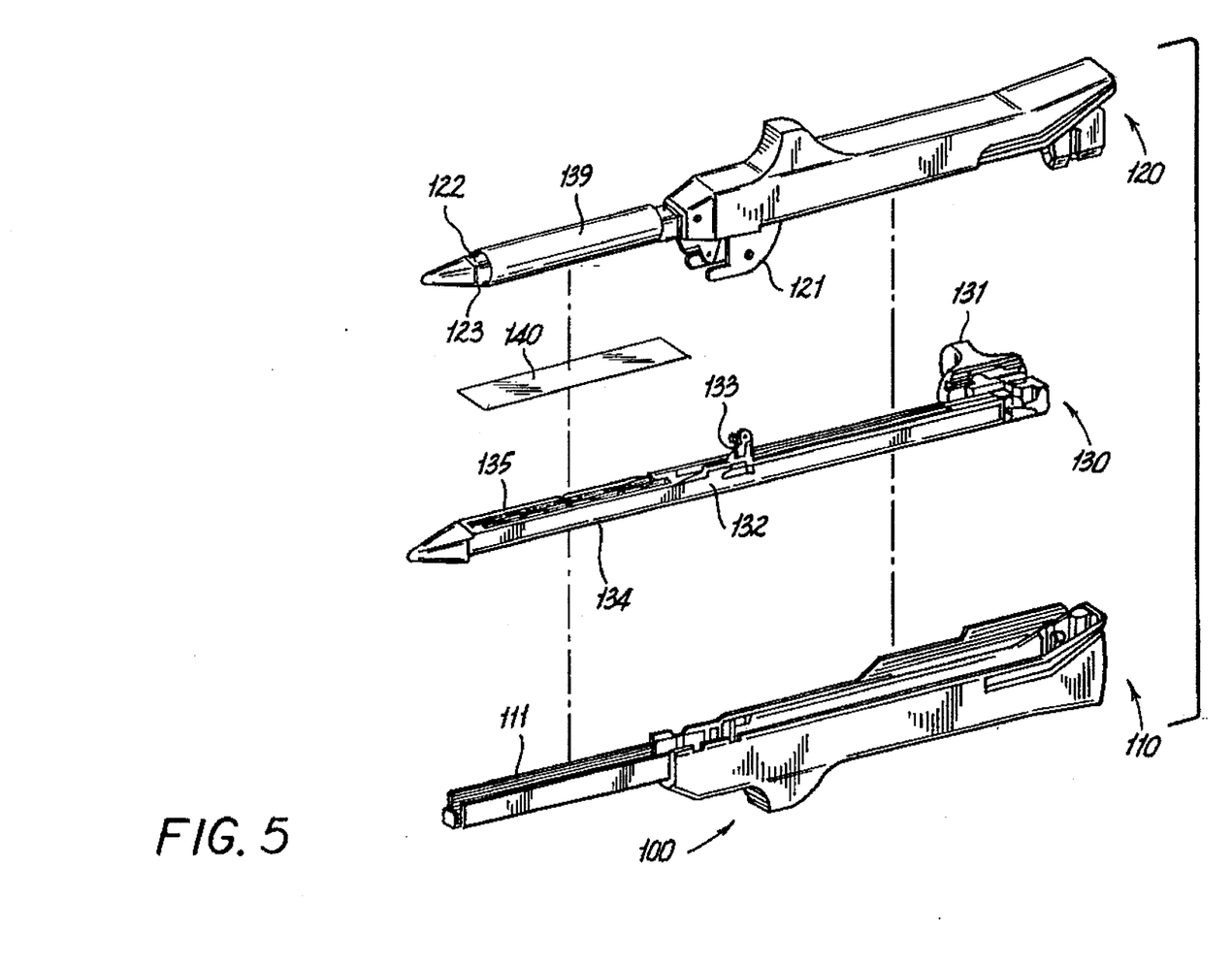
FIG. 5 is a perspective view depicting the separated parts of a surgical stapling apparatus having associated therewith a tubular shaped biocompatible surgical fabric positioned over the anvil assembly and a planar fabric positioned over the cartridge assembly of the apparatus.

As shown in FIG. 5, one or more individual pieces or segments of biocompatible surgical fabric can be employed in carrying out the present invention. Therefore, it is contemplated that two or more pieces or layers of fabric can be attached to a surgical stapling device as herein disclosed. For example, tubular fabric prosthesis 139 is fitted over anvil portion 122 and a planar fabric prosthesis 140 is attached to cartridge assembly 135 of stapling apparatus 100. In such a case, body tissue is sandwiched between and secured to both prostheses 139, 140, thereby providing fabric at both the entry and exit points of the staples or fasteners. The tubular prosthesis can be subsequently cut longitudinally along its longest axis to provide free ends which can be stapled or otherwise affixed to surrounding tissue and/or organs for further structural support.

Biocompatible surgical fabric 139, 140 can be woven, knit or nonwoven and can be bioabsorbable or nonbioabsorbable. Nonwoven bioabsorbable fabric is generally preferred in carrying out this invention. Bioabsorbable surgical fabrics include those fabricated from homopolymers, copolymers or blends obtained from one or more monomers selected from the group consisting of glycolide, glycolic acid, lactide, lactic acid, p-dioxanone, α-caprolactone and trimethylene carbonate. Bioabsorbable surgical fabrics, especially those that are nonwoven, manufactured from copolymers of glycolide and lactide are preferred. U.S. Pat. Nos. 3,875,937, 3,937,223 and 4,128,612 describe bioabsorbable surgical fabrics suitable for use with the present invention. Nonbioabsorbable surgical fabrics include those that are fabricated from such polymers as polyethylene, polypropylene, nylon, polyethylene terephthalate, polytetrafluoroethylene, polyvinylidene fluoride, and the like.

Fabric 139, 140 is releasably attached to either anvil assembly 123 or cartridge assembly 135 as shown in FIGS. 1–4 or either anvil assembly 218 or cartridge assembly 214 as shown in FIGS. 8 and 9. Alternatively, the anvil assembly and cartridge assembly can both have fabric disposed thereon (FIG. 5), in any combination of tubular and planar structure, to provide a tissue/fabric "sandwich" upon actuation of the instrument.

The attachment of the fabric to a surgical stapling device in accordance with this invention should be secure enough to prevent the fabric from slipping off the device, yet not be so strong as to inhibit separation of the fabric from the device after the device has been actuated. Such releasable attachment can advantageously be effected by employing a plurality of pins 141 as illustrated in FIGS. 1, 7 and 9. As shown in FIG. 6, a plurality of longitudinally spaced clips 142 may also be employed as the securing means. A combination of pins and/or clips can also be employed. The precise number and location of pins and/or clips is not critical so long as the surgical fabric is releasably attached to the stapling apparatus.

Operation of a surgical stapling apparatus falling within the scope of this invention is illustrated in FIG. 7. Cartridge assembly 135 includes pusher members 136 which are acted upon by slidably mounted cam bar 132. Upon movement of cam bar 132 in the direction indicated as "A", pusher members 136 exert an upwardly-directed force B on staples 137 housed in cartridge assembly 135. Staples 137 penetrate fabric 140 (secured to cartridge assembly 135 by a plurality of pins 141) and tissue layer 150. Thereafter, staples 137 strike anvil assembly 123 for closure. Following actuation, the stapling apparatus is withdrawn from the stapling site, thus leaving behind a fabric prosthesis stapled to body tissue with a plurality of rows of staples.

Fabric prosthesis 140 can act as an adhesion barrier, hemostatic agent, reinforcement, tissue growth enhancer, and the like. Furthermore, it shall be understood that fabric prosthesis 140 can have incorporated therein and/or thereon one or more medically and/or surgically useful substances such as drugs, enzymes, growth factors, peptides, proteins, dyes, diagnostic agents or hemostasis agents.

While this invention has been disclosed herein in connection with certain embodiments and certain structural and procedural details, it is clear that changes, modifications or equivalents can be used by those skilled in the art. For example, when a knife blade is used in conjunction with a surgical stapler, the fabric can be precut or weakened to facilitate passage of the blade between or through the fabric. Accordingly, such changes within the principles of this invention are intended to be included within the scope of the claims below.

What is claimed is:

1. A surgical apparatus for driving surgical fasteners into body tissue comprising:

first jaw structure for housing a plurality of surgical fasteners;

second jaw structure disposed in juxtaposed alignment with said first jaw structure and configured and dimensioned for effecting closure of said plurality of fasteners; and, at least one tubular biocompatible surgical fabric releasably attached to either of said first and second jaw structures by a plurality of pins and/or clips.

2. The apparatus of claim 1 wherein the fabric is selected from the group consisting of woven, knit and nonwoven fabric.

3. The apparatus of claim 1 wherein the fabric is selected from the group consisting of bioabsorbable and nonbioabsorbable fabric.

4. The apparatus of claim 1 wherein the fabric is fabricated from a bioabsorbable polymer comprising a homopolymer, copolymer or blend obtained from one or more monomers selected from the group consisting of glycolide, glycolic acid, lactide, lactic acid, p-dioxanone, α-caprolactone and trimethylene carbonate.

5. The apparatus of claim 1 wherein the fabric is fabricated from a copolymer of glycolide and lactide.

6. The apparatus of claim 7 wherein the fabric is nonwoven.

7. The apparatus of claim 1 wherein the fabric is fabricated from a nonbioabsorbable polymer selected from the group consisting of polyethylene, polypropylene, nylon, polyethylene terephthalate, polytetrafluoroethylene and polyvinylidenefluoride.

8. The apparatus of claim 1 wherein the fabric further comprises one or more substances selected from the group consisting of drugs, enzymes, growth factors, peptides, proteins, dyes, diagnostic agents or hemostasis agents.

9. The apparatus of claim 1 wherein said first jaw structure further comprises a knife.

10. The apparatus of claim 1 wherein the fabric is releasably attached to said first jaw structure.

11. The apparatus of claim 1 wherein the fabric is releasably attached to said second jaw structure.

12. The apparatus of claim 1 wherein at least one biocompatible surgical fabric is releasably attached to each of said first and second jaw structures.

13. A surgical apparatus for driving surgical fasteners into body tissue comprising:

first jaw structure for housing a plurality of surgical fasteners;

second jaw structure disposed in juxtaposed alignment with said first jaw structure and configured and dimensioned for effecting closure of said plurality of fasteners; and at least one biocompatible surgical fabric releasably attached to either of said first and second jaw structures by a plurality of pins.

\* \* \* \* \*